(12) United States Patent
Harada et al.

(10) Patent No.: US 9,165,356 B2
(45) Date of Patent: Oct. 20, 2015

(54) DEFECT INSPECTION METHOD AND DEFECT INSPECTION DEVICE

(75) Inventors: Minoru Harada, Tokyo (JP); Atsushi Miyamoto, Tokyo (JP); Takehiro Hirai, Tokyo (JP); Fumihiko Fukunaga, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 14/238,105

(22) PCT Filed: Jul. 6, 2012

(86) PCT No.: PCT/JP2012/067265
§ 371 (c)(1),
(2), (4) Date: Feb. 10, 2014

(87) PCT Pub. No.: WO2013/035419
PCT Pub. Date: Mar. 14, 2013

(65) Prior Publication Data
US 2014/0169657 A1    Jun. 19, 2014

(30) Foreign Application Priority Data
Sep. 9, 2011  (JP) .................................. 2011-196679

(51) Int. Cl.
*G06K 9/00* (2006.01)
*G06T 7/00* (2006.01)
*G01N 21/956* (2006.01)
(Continued)

(52) U.S. Cl.
CPC .............. *G06T 7/001* (2013.01); *G01N 21/956* (2013.01); *H01L 22/12* (2013.01); *H01L 22/20* (2013.01); *G01N 21/9501* (2013.01); *G01N 2021/8861* (2013.01); *G01N 2021/8867* (2013.01)

(58) Field of Classification Search
None
See application file for complete search history.

(56) References Cited

U.S. PATENT DOCUMENTS 7,873,202 B2    1/2011  Kurihara et al.
7,904,845 B2    3/2011  Fouquet et al.
(Continued)

FOREIGN PATENT DOCUMENTS

JP    2001-189358 A    7/2001
JP    2005-302906 A    10/2005
(Continued)

OTHER PUBLICATIONS

International Search Report (PCT/ISA/210) with English translation dated Aug. 28, 2012 (Eight (8) pages).
(Continued)

*Primary Examiner* — Daniel Mariam
(74) *Attorney, Agent, or Firm* — Crowell & Moring LLP

(57) ABSTRACT

A defect inspection method for inspecting a defect on a semiconductor wafer, using plural inspection methods includes: merging hot-spot coordinates as coordinates on the semiconductor wafer, designated by a user, or coordinates where a systematic defect can occur, with detected defect coordinates on the semiconductor wafer, acquired from inspection information, after information indicating the type of coordinates are added thereto; deciding an inspection sequence of the coordinates merged with each other; and defect inspection for executing selection using the information indicating the respective types of the coordinates merged with each other, and executing an inspection by selecting an inspection method for every coordinates to be inspected.

20 Claims, 15 Drawing Sheets

(51) Int. Cl.
*H01L 21/66* (2006.01)
*G01N 21/95* (2006.01)
*G01N 21/88* (2006.01)

(56) References Cited

U.S. PATENT DOCUMENTS

| | | | |
|---|---|---|---|
| 2003/0058435 A1* | 3/2003 | Honda et al. | 356/237.1 |
| 2005/0234672 A1 | 10/2005 | Takahashi et al. | |
| 2006/0238753 A1* | 10/2006 | Tsuji et al. | 356/237.2 |
| 2006/0284088 A1* | 12/2006 | Fukunaga et al. | 250/310 |
| 2007/0031026 A1 | 2/2007 | Kurihara et al. | |
| 2007/0236689 A1* | 10/2007 | Yoshida et al. | 356/237.2 |
| 2008/0163140 A1* | 7/2008 | Fouquet et al. | 716/4 |
| 2008/0232671 A1 | 9/2008 | Asano et al. | |
| 2008/0298669 A1 | 12/2008 | Funakoshi et al. | |
| 2011/0276935 A1* | 11/2011 | Fouquet et al. | 716/112 |

FOREIGN PATENT DOCUMENTS

| | | |
|---|---|---|
| JP | 2008-233687 A | 10/2006 |
| JP | 2007-40910 A | 2/2007 |
| JP | 2008-300670 A | 12/2008 |
| JP | 2010-85145 A | 4/2010 |

OTHER PUBLICATIONS

Japanese Office Action dated Feb. 18, 2014 (four (4) pages).

* cited by examiner

DANGER POINT INSPECTION
→ SHIFT A VISUAL FIELD — S501
→ CAPTURE POSITIONING IMAGES — S502
→ DETERMINE A POSITION OF A CAPTURED IMAGE — S503
→ CAPTURE AN IMAGE OF A DANGER POINT — S504
→ DETECT DEFECTS — S505
→ CLASSIFY THE DEFECTS — S506
→ END

CHIP COORDINATE SYSTEM

WAFER COORDINATE SYSTEM

FIG. 7

| # | CHIP COORDINATES | WAFER COORDINATES | | | | |
| --- | --- | --- | --- | --- | --- | --- |
| | | CHIP 1 | CHIP 2 | CHIP 3 | | CHIP k |
| 1 | $(cx_1, cy_1)$ | $(x_{11}, y_{11})$ | $(x_{12}, y_{12})$ | $(x_{13}, y_{13})$ | | $(x_{1k}, y_{1k})$ |
| 2 | $(cx_1, cy_1)$ | $(x_{21}, y_{21})$ | $(x_{22}, y_{22})$ | $(x_{23}, y_{23})$ | | $(x_{2k}, y_{2k})$ |
| m | $(cx_m, cy_m)$ | $(x_{m1}, y_{m1})$ | $(x_{m2}, y_{m2})$ | $(x_{m3}, y_{m3})$ | | $(x_{mk}, y_{mk})$ |

FIG. 8

| CAPTURED-IMAGE SEQUENCE | # | ATTRIBUTE | WAFER COORDINATES (CAPTURED-IMAGE POSITION COORDINATES) | STAGE-SHIFT COORDINATES |
| --- | --- | --- | --- | --- |
| 1 | 1 | DETECTED DEFECT | $(x_1, y_1)$ | $(x_1, y_1)$ |
| 2 | N | DETECTED DEFECT | $(x_N, y_N)$ | $(x_N, y_N)$ |
| i | 2 | DETECTED DEFECT | $(x_2, y_2)$ | $(x_i, y_i)$ |
| i+1 | N+1 | DANGER POINT | $(x_{N+1}, y_{N+1})$ | $(x_i, y_i)$ |
| i+2 | | DETECTED DEFECT | $(x_3, y_3)$ | $(x_3, y_3)$ |
| N+M | N+4 | DANGER POINT | $(x_{N+4}, y_{N+4})$ | $(x_{N+4}, y_{N+4})$ |

FIG. 9

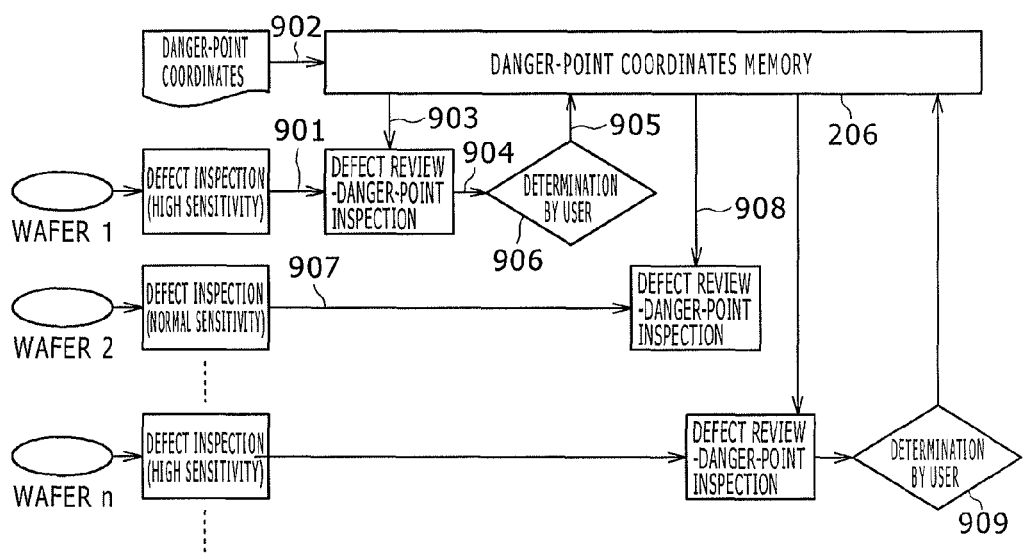

| # | COORDINATE | ATTRIBUTE | INCIDENTAL INFORMATION |
|---|---|---|---|
| 1 | $(x_1, y_1)$ | REFERENCE | CORRESPONDING DEFECT POINT #3 |
| 2 | $(x_2, y_2)$ | DANGER POINT | DEFECT STATE AND OCCURRENCE PROBABILITY $(\delta 21, p21), (\delta 22, p22) \cdots$ |
| 3 | $(x_3, y_4)$ | DEFECT | CORRESPONDING REFERENCE POINT #1 |
| 4 | $(x_4, y_4)$ | DEFECT | MEMORY CELL |
| ... | ... | ... | ... |
| n | $(x_n, y_n)$ | | |

DEFECT INSPECTION METHOD AND DEFECT INSPECTION DEVICE

BACKGROUND

The present invention relates to a method for observing and inspecting a defect that has occurred during the manufacture of a semiconductor product, and a defect inspection device using the same.

In order to secure earnings in the manufacture of a semiconductor wafer, it is important to quickly start up a manufacturing process thereof to thereby cause transition to a high-yield mass production system to take place at an early stage. For this purpose, various types of inspection • measurement devices are introduced into a production line. For the purpose of deciding a process condition enabling a desired circuit pattern to be formed at an early stage, a procedure has been in practice whereby a plurality of wafers or chips are prepared by intentionally varying, for example, a process condition in a process startup stage, an inspection is performed against the wafers or the chips, and a process condition is decided on the basis of a result of the inspection. Meanwhile, an inspection on a wafer in a mass production stage is performed for the purpose of process monitoring. More specifically, a sampling inspection of a wafer is performed in a stage halfway through the manufacture of the wafer to thereby examine whether or not a defect has occurred to the surface of the wafer, or whether or not abnormality is present on a circuit pattern formed on the surface of the wafer. If a defect or abnormality of the circuit pattern is detected as a result of the inspection, the cause thereof is looked into, and a necessary countermeasure is taken.

A defect observation device is a device for capturing a high-resolution image of detect coordinates of a wafer, using the output of the other inspection device, thereby outputting the image. Since progress has since been made in the miniaturization of a semiconductor manufacturing process to be accompanied by a defect size reaching to the order of several tens of nm, resolution on the order of several nm is required in order to observe a defect in detail. For this reason, an observation device (hereinafter referred to as a Review SEM) using a scanning electron microscope (SEM) has lately been in widespread use. A method for detecting a defect by comparing a captured-image of a defective site with an image of a non-defective product is described in Japanese Unexamined Patent Application Publication No. 2001-189358. Further, a method for detecting a defect from one sheet of an image that has captured a defective site, is described in Japanese Unexamined Patent Application Publication No. 2007-40910.

A method for deciding coordinates on a wafer, the coordinates being those to be reviewed between defect reviews, in an inspection device having not less than two inspection systems, is described in U.S. Pat. No. 7,904,845.

SUMMARY

In order to produce a semiconductor wafer at a high yield, it is important to get hold of an occurrence frequency for every defect types occurring in a production process, and identify the cause of occurrence of a fatal defect to be subsequently fed back.

As a result of the progress made in the miniaturization of the semiconductor manufacturing process, a fatal defect has turned more microscopic in size. Further, a defect includes a random defect, and a systematic defect. The random defect has variation in respect of occurrence frequency, defect state, and defect magnitude, and an occurrence-location thereof is unpredictable. In the case of the systematic defect, a location susceptible to occurrence is attributable to a circuit pattern, and so forth, so that the location is often constant. However, there can be the case where the systematic defect does not occur, in which case, it is difficult to determine whether or not a pattern state is defective as compared with the case of the random defect.

Accordingly, if an optical inspection device is set so as to have sensitivity capable of detecting a microscopic defect, this will create a problem of detecting manufacturing tolerance, noise, and so forth, which do not represent a defect, on a massive scale.

Since an image in high-resolution can be acquired using the SEM, a microscopic defect can be detected in high-resolution, however, it takes time to capture the image as compared with the case of using the optical inspection device, so that it is not practical to inspect the whole surface of a wafer, so that deterioration in throughput poses a problem.

In this connection, the coordinates of the systematic defect are predicted in the method according to U.S. Pat. No. 7,904,845, however, a method for resolving the problem described as above has not been disclosed.

It is therefore an object of the invention to provide an inspection method capable of striking a balance between high throughput and capture rate of a defect in the case of executing a defect inspection including a defect review using an optical inspection device, and a fixed-point inspection using an SEM.

To that end, according to one aspect of the present invention, there is provided a method for inspecting a defect on a semiconductor wafer, using a plurality of inspection methods. The method includes merging hot-spot coordinates as coordinates on the semiconductor wafer, where a systematic defect can occur, with detected defect coordinates on the semiconductor wafer, acquired from other inspection device output information, after information indicating a type of coordinates is added thereto; deciding an inspection sequence of the coordinates merged with each other; and defect inspection for executing selection using the information indicating respective types of the coordinates merged with each other, and executing an inspection by selecting an inspection method for every coordinates to be inspected.

According to the aspect of the present invention, a highly accurate inspection can be carried out at high throughput in the case of executing the defect review, and the fixed-point inspection.

BRIEF DESCRIPTION OF THE DRAWINGS

FIG. 7 is a view showing a relationship of chip coordinates corresponding to wafer coordinates by way of example;

FIG. 8 is a view showing an example of a result of setting captured-image sequences of detected defect coordinates and hot-spot coordinates;

FIG. 9 is a view showing a method for deciding a hot-spot on the basis of a hot-spot candidate;

DETAILED DESCRIPTION

First Embodiment

An image auto-classification device according to a first embodiment of the invention is hereinafter described. With the present embodiment, there is described the case of classifying images captured by an observation device provided with a scanning electron microscope (SEM); however, an imaging device of the invention may be a device other than the SEM, and may be an imaging device using a charged particle beam such as ion, and so forth.

Figure 1:
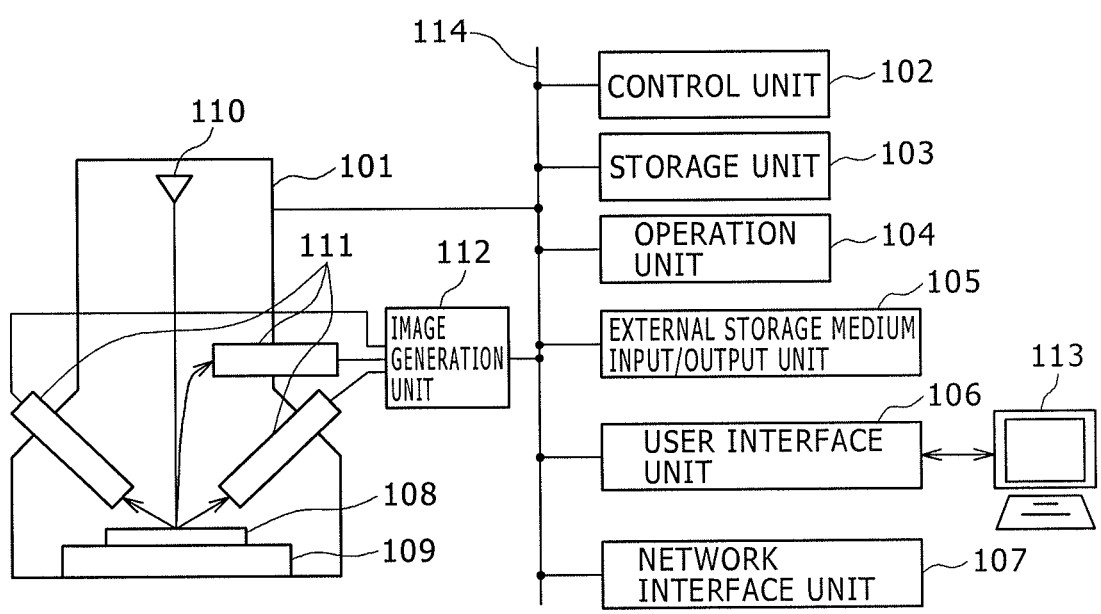
FIG. 1 is a block diagram of a defect inspection device.

FIG. 1 is a block diagram showing the auto-classification device according to the first embodiment of the invention. The device is made up of an SEM 101 for capturing an image, a control unit 102 for executing overall control, a storage unit 103 for storing information in a magnetic disc, a semiconductor memory, and so forth, an operation unit 104 for executing an operation according to a program, an external storage-media input-output unit 105 for executing input-output of information with external storage-media connected to the device, a user interface unit 106 for controlling input-output of information with a user, and a network interface unit 107 for executing communications with other devices and so forth, via a network. Further, an input-output terminal 113 made up of a keyboard, mouse, display, and so forth is connected to the user interface unit 106. The SEM 101 is made up of a movable stage 109 for mounting a specimen wafer 108 thereon, an electron source 110 for irradiating the specimen wafer 108 with an electron beam, and a detector 111 for detecting a secondary electron, reflection electron, and so forth, emitted from the specimen wafer 108. In addition to those components, the SEM 101 is provided with an electron lens (not shown) for causing the electron beams to be converged on the specimen, a deflector (not shown) for causing the electron beam to scan over the specimen wafer, an image generation unit 112 for generating a digital image through digital conversion of a signal from the detector 111, and so forth. Further, these constituents are connected with each other via a bus 114, being capable of executing mutual exchange of information.

Figure 2:
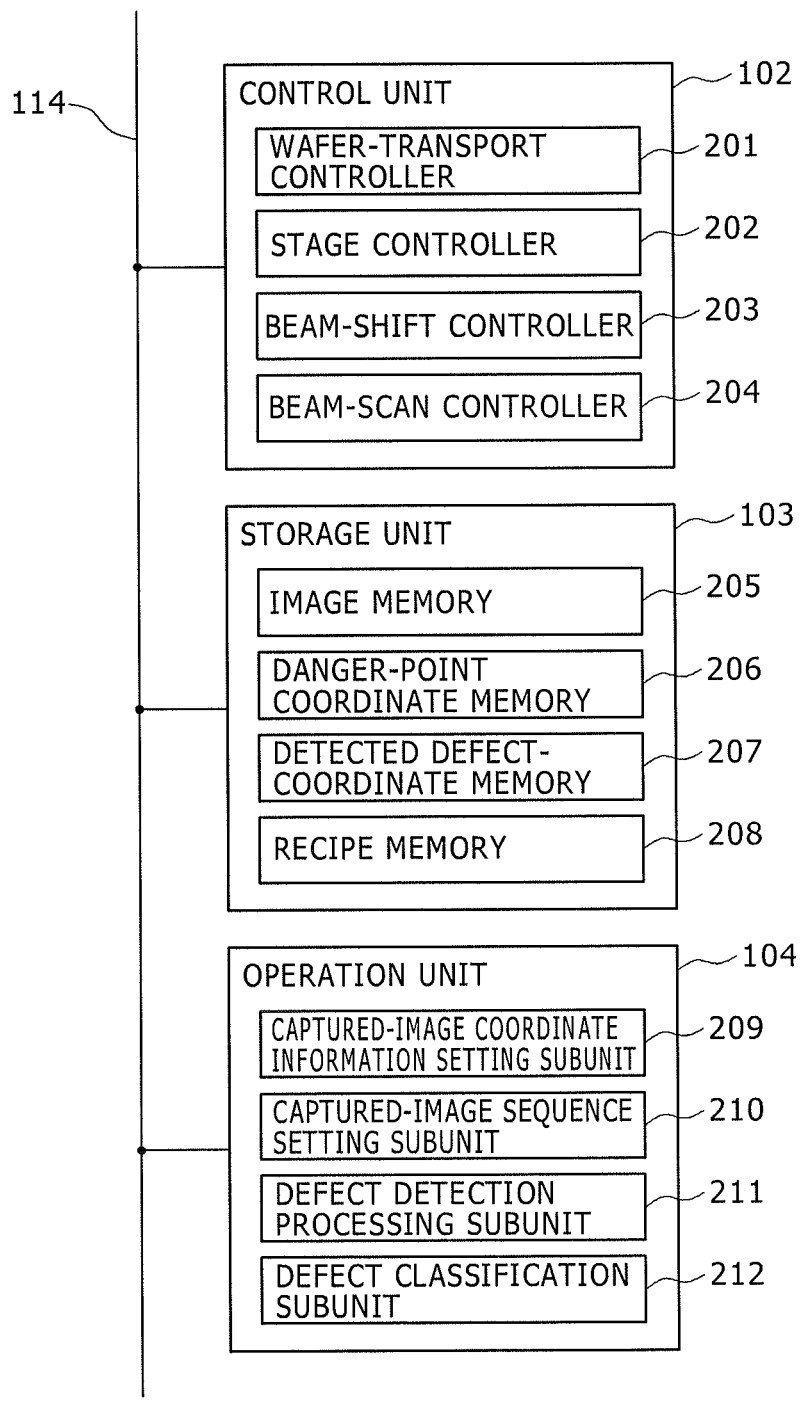
FIG. 2 is a block diagram showing part of the defect inspection device including a control unit, a storage unit, and an operation unit.

FIG. 2 is a block diagram showing the control unit 102, the storage unit 103, and the operation unit 104, respectively. The control unit 102 is made up of a wafer-transport controller 201 for controlling wafer-transport, a stage controller 202 for controlling the stage, a beam-shift controller 203 for controlling an irradiation location of the electron beam, and a beam-scan controller 204 for controlling scanning with the electron beam. The storage unit 103 is made up of an image memory 205 for storing image-data as acquired, a hot-spot coordinate memory 206 for storing the coordinates of a hot-spot, a detected defect-coordinate memory 207 for storing defect-coordinates detected by the other inspection device, and a recipe memory 208 for storing a defect review and parameters of a fixed-point inspection, and so forth. The operation unit 104 is made up of a captured-image coordinate information setting subunit 209 for setting information on captured-image coordinates, a captured-image sequence setting subunit 210 for setting a captured-image sequence, a defect detection processing subunit 211 for detecting a defect site, and a defect-classification subunit 212 for classifying defects on a type-by-type basis. Further, those subunits 209 through 212 may be each configured as a hardware piece designed so as to perform each operation, however, those subunits may be alternatively configured such that each operation can be executed using a general-purpose processing unit (for example, CPU, GPU, and so forth) installed as software.

A method for acquiring an image of designated coordinates is described hereinafter. First, the wafer 108 as a target for a captured-image is placed on the stage 109 by a robot arm controlled by the wafer-transport controller 201. Then, the stage 109 is moved by the stage controller 202 such that an image-capture visual field is included in a beam-irradiation range. At this point in time, measurement of a stage position is executed in order to absorb a shift-error of the stage, and the irradiation location of the electron beam is adjusted by the beam-shift controller 203 in such a way as to cancel the shift-error out. The electron beam is emanated from the electron source 110 so as to scan inside the image-capture visual field by the action of the beam-scan controller 204. The secondary electron as well as the reflection electron, emitted from the wafer, due to irradiation with the beam, are detected by the detector 111 to be turned into a digital image through the image generation unit 112. A captured-image, together with incidental information such as an image-capture condition, an image-capture date, and so forth, is stored in the image memory 205.

Figure 3:
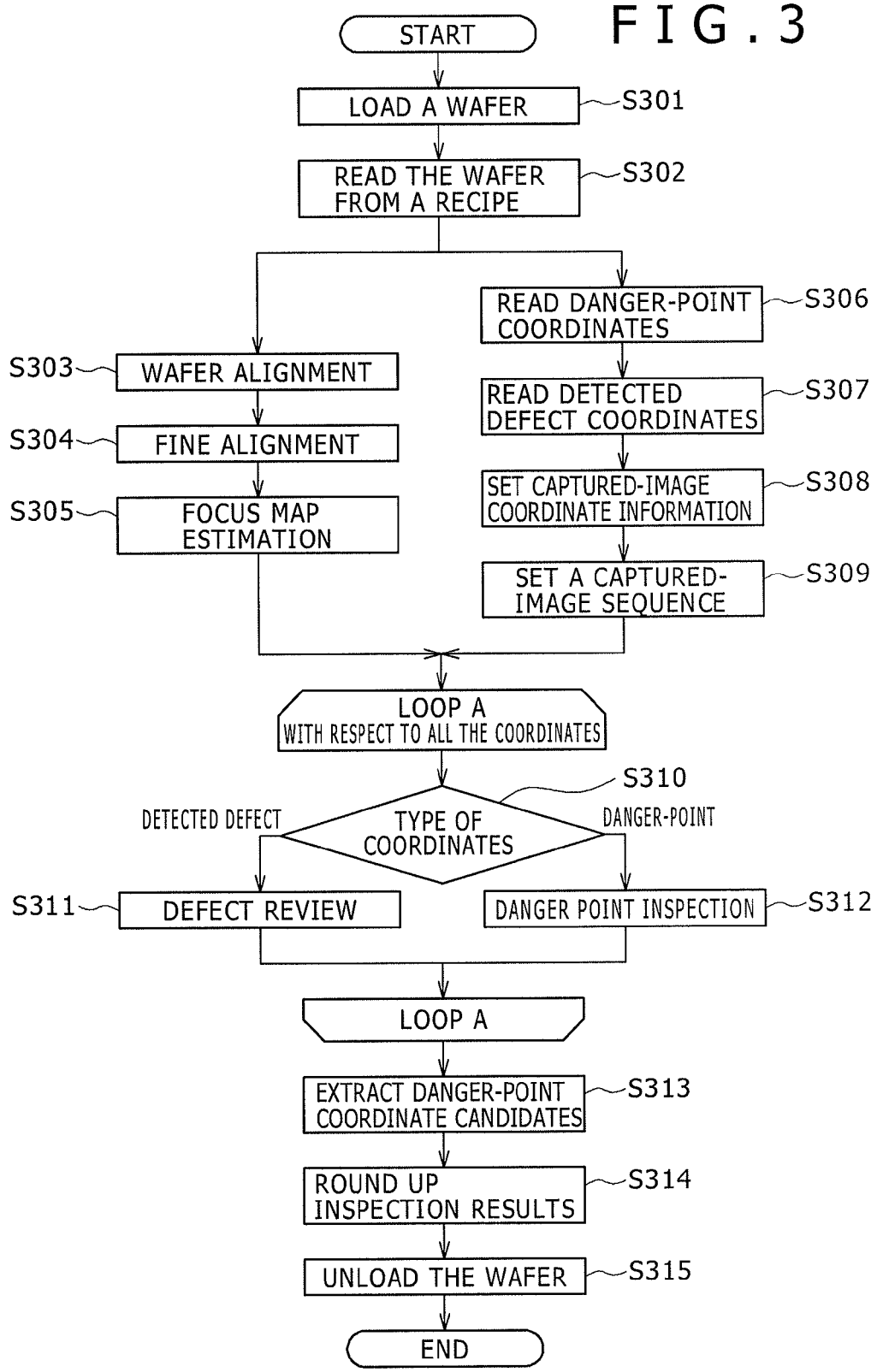
FIG. 3 is a view showing a processing flow for defect inspection.

FIG. 3 is a view showing a flow for executing a defect review, and a hot-spot inspection, according to the invention. First, a wafer is loaded on the stage (step S301), and a recipe corresponding to the wafer is read from the recipe memory 208 (step S302). The recipe stores parameters concerning wafer alignment (step S303), fine alignment (step S304), focus map estimation (step S305), defect review (step S311), and hot-spot inspection (step S312). The recipe is read, and subsequently, the wafer alignment (step S303), the fine alignment (step S304), and the focus map estimation (step S305) are each executed. Next, hot-spot coordinates corresponding to the wafer are read (step S306), and reads detected defect coordinates as outputted from other inspection device (step S307). Then, the hot-spot coordinates are merged with the detected defect coordinates, after adding respective attributes thereto (step S308). Herein, by "a hot-spot" is meant a location where a systematic defect can occur. At the time of merging, information indicating the type of coordinates is added to the hot-spot coordinates, and detected defect coordinates, respectively, and in this case, the information, in particular, is referred to as an attribute. Then, the captured-image sequence is rearranged such that a shift distance of the stage is rendered shorter (step S309). Further, processing for the wafer alignment (step S303) through the focus map estimation (step S305) may be executed in parallel with processing for the hot-spot coordinates reading (step S306) through the captured-image sequence setting (step S309). Still further, with respect to the fine alignment (the step S304), the focus map estimation (the step S305), the presence/absence of execution may be changed over according to the recipe.

Reverting to FIG. 3, further description is given hereinafter. With respect to all the coordinate points that are set by processing for the captured-image coordinate information setting (the step S308), the defect review, and the hot-spot inspection are each executed according to the captured-image sequence as set. At this point in time, the sequence is changed over on the basis of the attribute set to the coordinates (step S310). More specifically, if the attribute of the coordinates is "detected defect", a defect review sequence is executed (step S311). If the attribute of the coordinate is "hot-spot", a hot-spot inspection sequence is executed (step S312). Further, if an image-capture condition (for example, a probe current, an accelerating voltage, and so forth) stored in the recipe regarding the defect review and the hot-spot inspection does not match up with the present image-capture condition, the image-capture condition is changed over prior to execution of the sequence. After completion of the processing for all the coordinates, the hot-spot coordinate candidates are extracted (step S313), thereby summing up a result of the defect review, and a result of the hot-spot inspection (step S314). For example, occurrence frequency, and occurrence tendency in a wafer plane are summed up for every defect types. Finally, the wafer is unloaded (step S315), whereupon the flow is completed.

Figure 4:
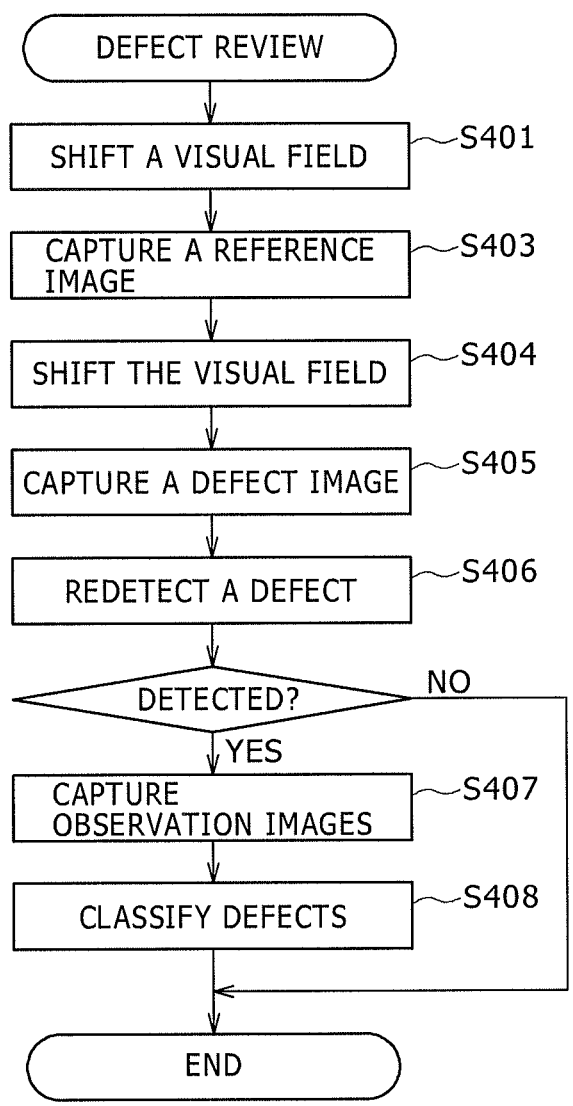
FIG. 4 is a view showing a processing flow for defect inspection (defect review)

The sequence of the defect review, using a comparative inspection, is described hereinafter with reference to FIG. 4. In the defect review, there are executed capturing of an observation image for use in observation of the external appearance of a defect, and defect classification based on the cause of defect occurrence, and the type of a defect. First, a visual field is shifted to a position where a reference image for use in the comparative inspection can be captured (step S401). More specifically, a shift of the stage, and a shift of the beam, as previously described, are executed. Then, the reference image is captured (step S403). Next, the visual field is shifted to a position where an image of the detected defect coordinates can be captured (step S404), thereby capturing a defect image (step S405). The reference image as captured is compared with the defect image to thereby execute redetection of a defect site (step S406). If defects are detected as a result of this redetection, observation images with respect to respective defect sites are captured (step S407) to classify defects on a type-by-type basis (step S408). The sequence of the defect review, using a comparative inspection, is described as above, by way of example. However, there may be used the method for detecting the defect from a defect image, as described in Japanese Unexamined Patent Application Publication No. 2007-40910. Further, the observation images may be captured on the basis of the detected defect coordinates without execution of redetection of defects to thereby execute classification. These observation images can be changed over on the basis of the parameters stored in the recipe. Further, the images as captured may be kept stored, and classification processing (the step S408) may be comprehensively carried out later on.

Figure 5:
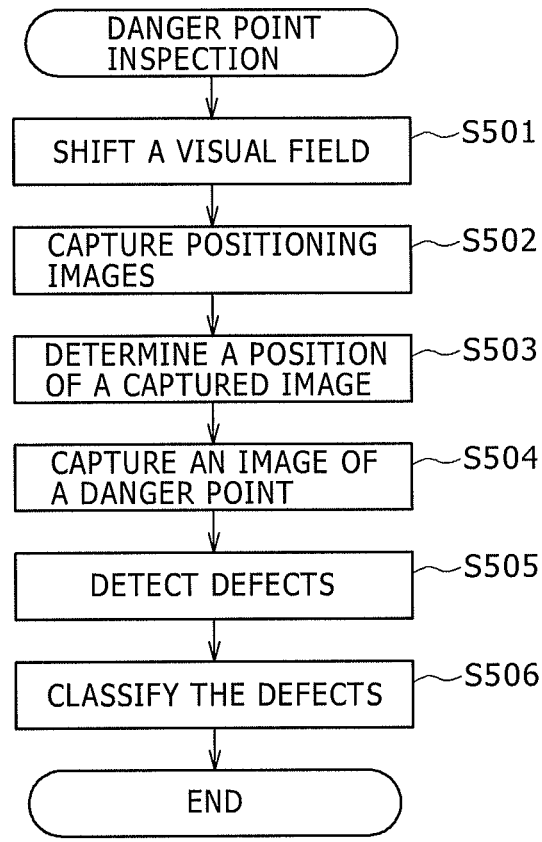
FIG. 5 is a view showing a processing flow for hot-spot inspection.

The sequence of the hot-spot inspection is described hereinafter with reference to FIG. 5. In the hot-spot inspection, hot-spot images are captured, and defect sites are detected from the captured-images, whereupon respective defect sites as detected are classified for every defect types. For this purpose, a visual field is first shifted to a position where the image of a hot-spot can be captured (step S501). At this point in time, there can be the case where misregistration on the order of from several tens of nm to several μm occurs due to an error in measurement of a stop-position of the stage. Accordingly, a positioning image is captured (step S502), and a position of a template pattern with known relative coordinates against a preregistered hot-spot coordinates is identified from among the positioning images to thereby determine a position of a captured image (step S503), and capture an image of a hot-spot (step S504). Further, detection of defects (step S505), and classification of the defects (step S506) are executed on the basis of the image.

Further, if the misregistration is insignificant, there is no need for executing the capturing of the positioning images (the step S502), and the determination on the position of the captured-image (the step S503). The parameters stored in the recipe can be substituted for these steps. Further, the captured-image of a hot-spot may be kept stored, and the detection of defects (step S505), and the classification of the defects (step S506) may be comprehensively carried out later on.

Figure 6:
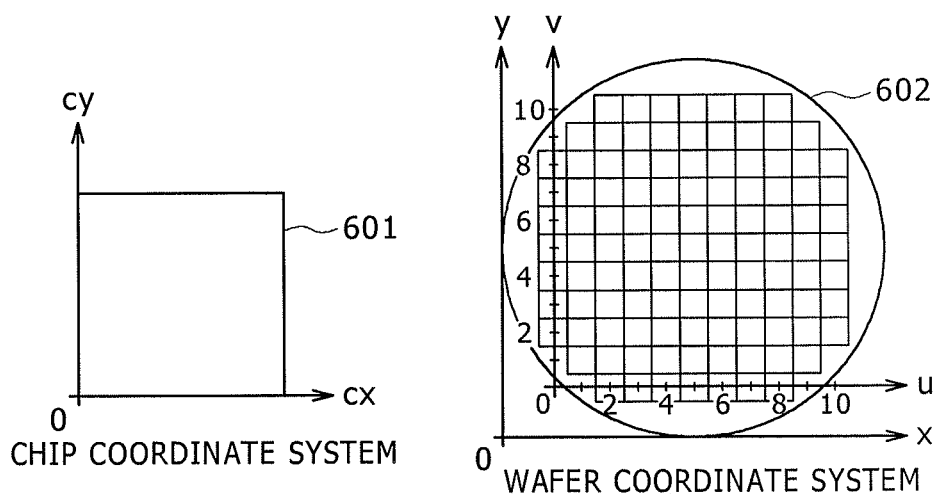
FIG. 6 is a view showing a chip coordinate system, and a wafer coordinate system.

Next, setting of the captured-image coordinate information (the step S308) is described hereinafter. This processing is a processing whereby the detected defect coordinates as inputted are merged with the hot-spot coordinates, after adding respective attributes thereto. The detected defect coordinates are defect coordinates that are detected by the other inspection device. Further, the detected defect coordinates as an input may be the result of sampling executed in advance, or the detected defect coordinates that are inputted may be sampled before the merging. The hot-spot coordinates are coordinates of a hot-spot where a user wants to execute inspection, such as a location where the systematic defect is susceptible to occurrence, and so forth. In general, the hot-spot is often designated in a chip coordinate system. FIG. 6 depicts a chip 601 on a semiconductor wafer, and a wafer 602. A chip coordinate system is a coordinate system where one point on a chip is the origin thereof, and a wafer coordinate system is a coordinate system where one point on a wafer is the origin thereof. A plurality of chips are normally laid out on a wafer, and a relationship between chip coordinates (cx, cy) of a chip at a position (u, v) and wafer coordinates (x, y) is represented by (formula 1), enabling mutual conversion to be executed with ease: provided that W, H express width, and height of one chip, respectively, whereas $o_x$, $o_y$ each express an offset.

$$\begin{pmatrix} x \\ y \end{pmatrix} = \begin{pmatrix} u \\ v \end{pmatrix}(W \quad H) + \begin{pmatrix} cx \\ cy \end{pmatrix}\begin{pmatrix} o_x \\ o_y \end{pmatrix} \quad \text{(Formula 1)}$$

FIG. 7 shows an example of a result of working out m pieces of hot-spot coordinates $(cx_i, cy_i)$ (i=1 through m) inputted in the chip coordinate system, together with hot-spot coordinates $(x_{ij}, y_{ij})$ (i=1 through m, j=1 through k) in the wafer coordinate system, on the basis of k pieces of chips designated as an inspection target.

Now, description reverts to the setting of the captured-image coordinate information (the step S308). After conversion of the hot-spot coordinates in the chip coordinate system into those of the wafer coordinate system by the method describe as above, the hot-spot coordinates are merged with the detected defect coordinates. In this case, the respective attributes are added thereto such that the detected defect coordinates are distinguished from the hot-spot coordinates.

In the step of the captured-image sequence setting (step S309), the captured-image sequence is rearranged such that shift-time of the stage becomes shorter with respect to the coordinates that are merged. The shift-time of the stage accrues from a shift distance of the table, and the shift-time of the stage includes the shift distance of the table. In general, a stage-shift takes time, so that the shorter the shift-time of the stage is, the higher will be a throughput-enhancement effect. However, since this problem is a combinational optimization problem, if the number of the hot-spots increases, it will become difficult to look for the optimal solution whereby the shift time is rendered the shortest within practical time. Accordingly, a quasi-optimal solution may be found using a simulated annealing method, and so forth. Further, if captured-image coordinates of plural points are present within a range where the coordinates can be shifted by a beam shift, the respective shift coordinates of the stage may be merged with each other, thereby causing a visual field to be shifted using the beam shift. Further, if the image-capture condition (for example, the probe current, the accelerating voltage, and so forth) at the time of capturing the image of the hot-spot coordinates differs from that at the time of capturing the image of the detected defect coordinates, a combination may be made such that time required for change-over is included in the shift-time from the hot-spot coordinates to the detected defect coordinates to thereby solve an optimization problem. More specifically, the shift time between coordinates identical in attribute to each other includes only time required for shifting of the stage, whereas the shift time between coordinates differing in attribute from each other includes time required for change-over of image-capture time in addition to the time required for the shifting of the stage. However, if the shifting of the stage can be executed in parallel with the change-over of the image-capture condition, longer time is regarded as the shift time. By so doing, the shift sequence can be decided after taking time for the change-over of the image-capture condition into consideration, thereby enabling the image-capture time in whole to be shortened.

FIG. 8 shows a result of setting the captured-image sequence with respect to the detected defect coordinates at N points, and the hot-spot coordinates at M points by way of example. In FIG. 8, there is shown an example of a result of sharing of stage-shift coordinates $(x_i, y_j)$ by taking the case of an i-th point of the captured-image coordinates $(x_2, y_2)$, and an (i+1)-th point of the captured-image coordinates $(x_{N+1}, y_{N+1})$ being within a range where these coordinates can be shifted by a beam shift.

Figure 10:
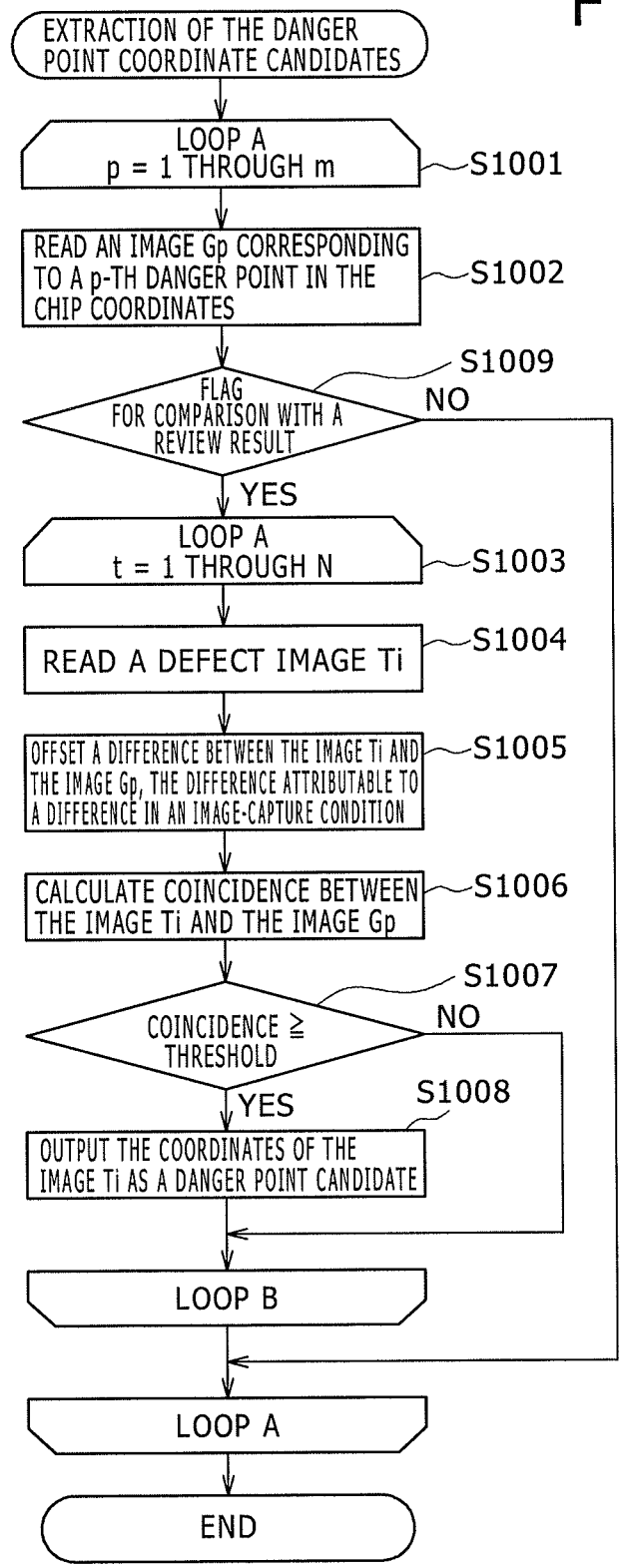
FIG. 10 is a view showing a processing flow for extracting a hot-spot candidate from a defect review result.

Next, in connection with the extraction of the hot-spot coordinate candidates (the step S313), an overall flow for extracting the hot-spot on the wafer is first described using the present function with reference to FIG. 9, and subsequently, the processing contents of the present process are described with reference to FIG. 10.

First, the flow for extracting the hot-spot on the wafer is described with reference to FIG. 9. A defect inspection using the other inspection device is applied to a first sheet of plural sheets of wafers, as an inspection target, after sensitivity thereof is raised. As a result, it has turned out that detected defect coordinates 901 include a random defect, a systematic defect, and massive nuisance defects. The random defect has variation in respect of occurrence frequency, defect state, and defect magnitude, and an occurrence-location thereof is unpredictable. In the case of the systematic defect, a location susceptible to occurrence is attributable to a circuit pattern, so that the location is often constant. However, there can be a case where the systematic defect does not occur at all, in which case, it is difficult to determine whether or not a pattern state is defective as compared with the case of the random defect. If an optical inspection device is set so as to have sensitivity capable of detecting a microscopic defect, this can possibly detect manufacturing tolerance, noise, and so forth, other than a defect, on a massive scale, representing the case where those other than a defect are erroneously detected as a defect.

Further, hot-spot coordinates 902 extracted from design information, and user's experience are kept stored in advance. Then, the defect review and the hot-spot inspection are executed according to the flow shown in FIG. 3 upon inputting of the detected defect coordinates 901, and hot-spot coordinates 903 as stored. By so doing, hot-spot coordinate candidates 904 are outputted. A user determines a hot-spot 905 from among the hot-spot coordinate candidates (step S906) and the hot-spot 905 is additionally stored. With a second sheet of the wafers, and onwards, the sensitivity of the other inspection device may be set to sensitivity capable of reducing occurrence of the nuisance defect, while detecting the random defect. In this case, a detection result of a minute systematic defect is not included in an inspection result 907; however, hot-spots 908 including the hot-spot extracted from the first wafer can be inspected, so that observation of a random defect, and inspection of a systematic defect can be conducted at high efficiency and at a high capture rate. Further, the determination on the hot-spot need not be performed only against the first sheet of the wafer, and the determination on the hot-spot may be performed at appropriate timing (step S909).

Figure 11A:
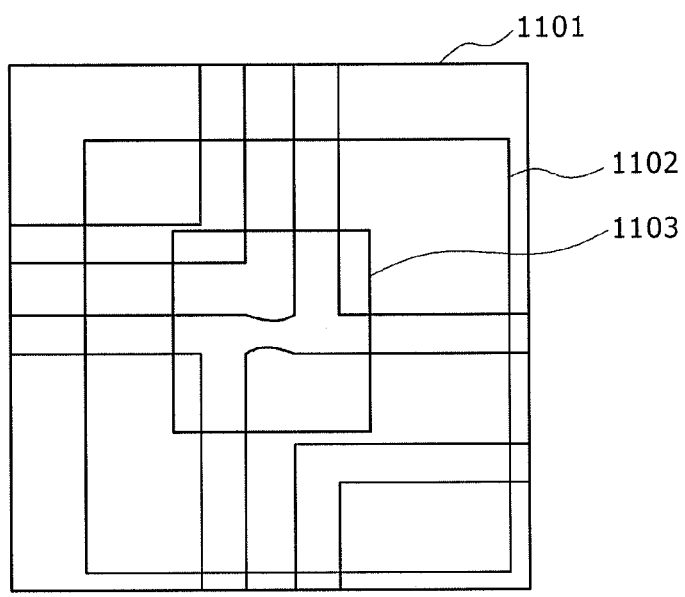
FIGS. 11A, 11B, and 11C show a difference in image due to a difference in image-capture condition.
Figure 11B:
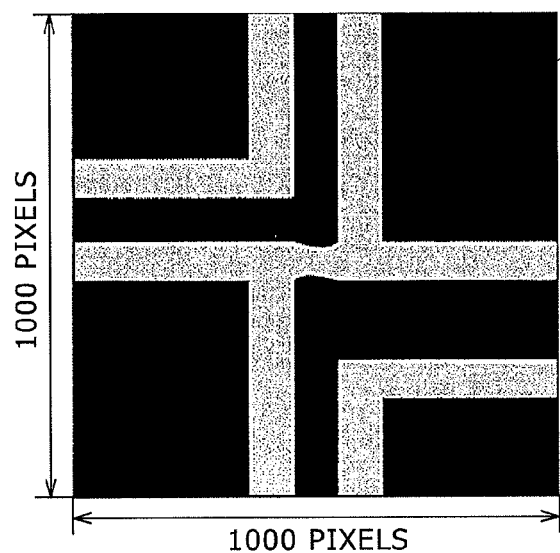
Figure 11C:
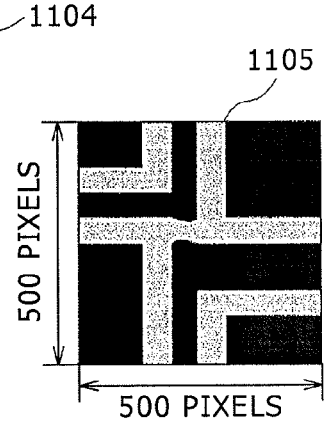

The contents of processing for the hot-spot coordinate candidates extraction (the step S313) are described hereinafter with reference to FIG. 10. The present processing is a processing for extracting the systematic defect candidates from among images collected in the defect review sequence. If the image is an image where there is formed the same circuit pattern as that in the case of the image collected in the hot-spot inspection sequence, and the same type of defect has occurred, a defect is determined as a systematic defect. Accordingly, a p-th image is first read from among hot-spot images at m locations in the chip coordinate system (step S1002). In this connection, there is the case where it is unnecessary to extract new hot-spot coordinates because identical circuit patterns are formed at hot-spots in, for example, a memory cell. Therefore, determination is made on whether or not comparison with a defect review image is made (step S1009). A user may designate whether or not comparison with a defect review image is made with respect to each hot-spot, or repeat periodicity of the circuit pattern may be determined from captured-images, and if the repeat periodicity exists, comparison may be suspended. Subsequently, a t-th defect image is read from among the defect review images captured at N locations, respectively (step S1004). Since there can be a difference in the image-capture condition, such as magnification and so forth, between the hot-spot image and the defect image, the images are each processed so as to absorb the difference in the image-capture condition in order to facilitate comparison of the images (step S1005). An example of the case where image-accommodation is required is described hereinafter with reference to FIGS. 11A to 11C. FIG. 11A shows an example of a relationship among a captured-image visual field 1101 of an image in the hot-spot inspection, a captured-image visual field 1102 of a defect image in the defect review, and a captured-image visual field 1103 of an observation image. FIG. 11B shows a hot-spot image as captured, and FIG. 11C shows a defect image. In this example, there is shown the case where the hot-spot image is captured so as to have 1000×1000 pixels, and the defect image is captured so as to have 500×500 pixels. Since the captured-image visual field, and an image size each can be individually set by the recipe, processing, such as scaling up, scaling down, clipping, and so forth, is applied to the images to thereby absorb the difference in the image-capture condition. Further, processing, such as noise removal, a super-resolution process, and so forth, may be applied. Now, reverting to FIG. 10, the description is continued. After completion of the image accommodation, a coincidence between the hot-spot image and the defect image is worked out (step S1006). In order to calculate the coincidence, it need only be sufficient to use, for example, a normalized correlation value. Further, a circuit pattern, and the contour of a defect may be detected from the images to thereby calculate the coincidence of the contour. Still further, the coincidence may be worked out by taking respective classification results of defect classification in the defect review (the step S408), and defect classification in the hot-spot inspection (the step S506) into consideration. If, for example, the classification results are identical to each other, the coincidence may be raised. Further, a defect classified as a foreign matter is determined as lower in the coincidence. The coincidence as worked out is compared with a preset threshold (step S1007), and if the coincidence is not less than the threshold, coordinates where the defect image is captured are outputted as a candidate of the hot-spot coordinates (step S1008). The steps S1004 through S1008 are executed against all the defect images (the step S1003) and the steps S1002 through S1008 are executed against all the hot-spot images (the step S1001). Further, the hot-spot image that is read in the step S1002 may be synthesized from plural sheets of the hot-spot images with respect to the chip coordinates p {the respective hot-spot images at the wafer coordinates $(x_{pj}, y_{pj})$ (j=1 through k), as shown in FIG. 7}. Further, the image that is read in the step S1004 may be the reference image instead of the defect image, or the reference image synthesized from the defect image.

Figure 12:
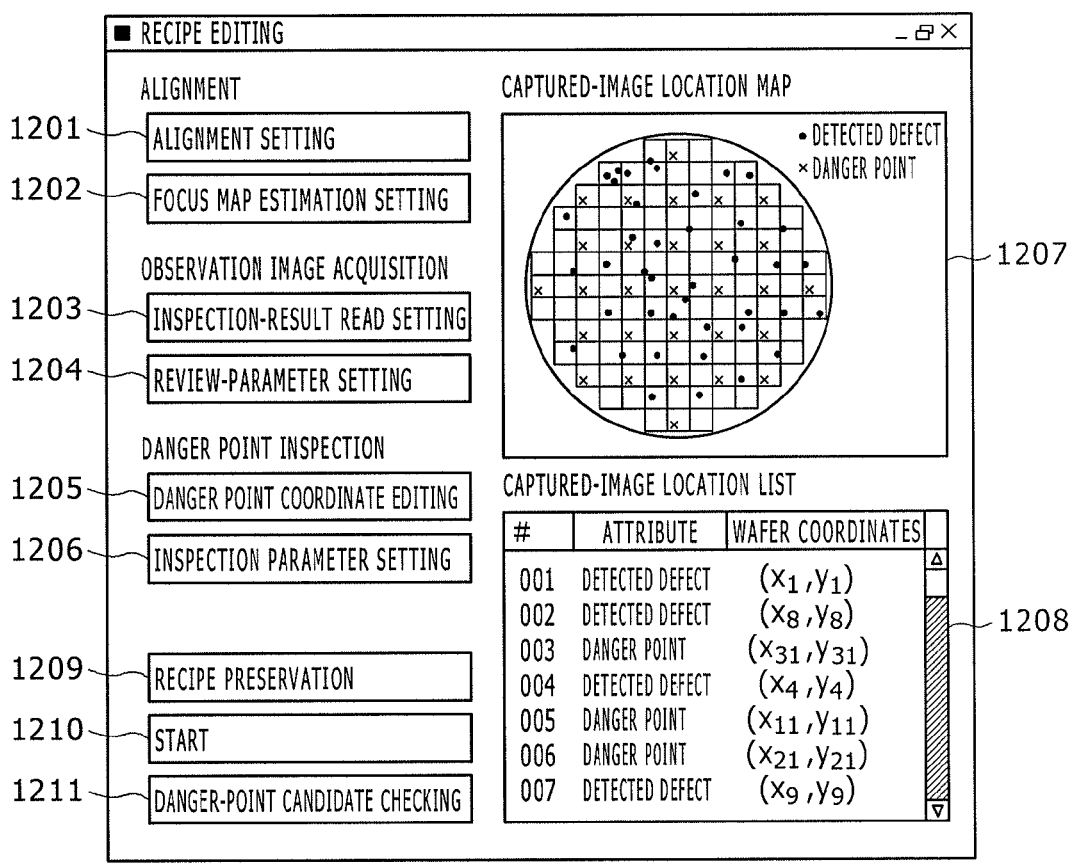
FIG. 12 is a view showing an example of an interface concerned with recipe editing.

A user interface according to the invention is henceforth described. FIG. 12 shows one example of the user interface concerned with setting of the recipe for execution of the defect review, and the hot-spot inspection. The present user interface is provided with a button 1201 for calling up a parameter-setting interface concerning the wafer alignment, and the fine alignment, and a button 1202 for calling up a parameter-setting interface concerning the focus map estimation. In addition, the user interface is provided with a button 1203 for designating a location where a result of inspection on a target wafer, conducted by the other inspection device, is stored, and a button 1204 for calling up a parameter-setting interface concerning a defect review recipe. Further, the user interface is provided with a button 1205 for calling up a hot-spot coordinate editing interface (described later on), and a button 1206 for calling up a parameter-setting interface concerning the hot-spot inspection. And there are further provided an interface 1207 where a result of reading detection defect coordinates, as set, and hot-spot coordinates are plotted on a wafer map to be displayed, and an interface 1208 for displaying a location list of captured-image coordinates, and attributes added thereto. There are further provided a button 1209 for preserving a recipe as prepared, a button 1210 for use in execution of the recipe, and a button 1211 for calling up an interface for checking hot-spot candidates after the execution of the recipe.

Figure 13:
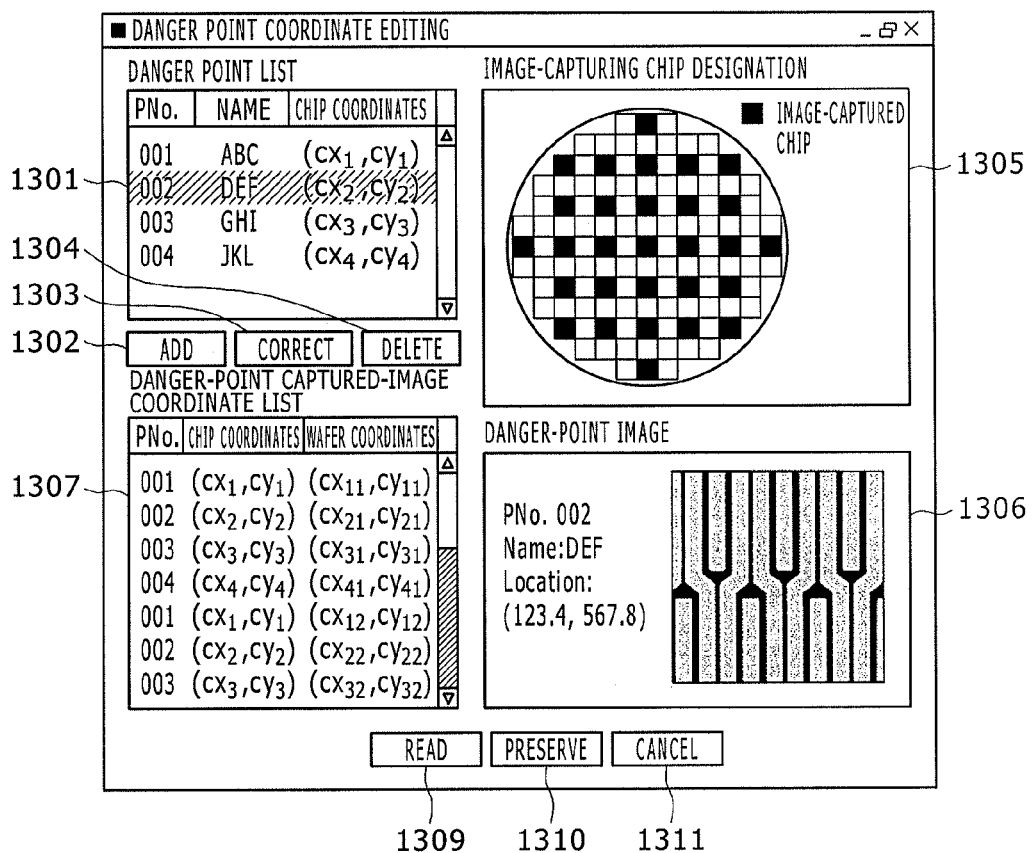
FIG. 13 is a view showing an example of an interface concerned with hot-spot coordinate editing.

FIG. 13 shows one example of an interface for use in hot-spot coordinate editing. The present interface is called up by "the hot-spot coordinate editing" button 1205 of the interface concerned with the recipe setting. The present interface is provided with an interface 1301 for displaying a list of respective chip coordinates at registered hot-spots, a button 1302 for calling up an interface for use in registration of new hot-spots, a button 1303 for calling up an interface for use in correction of the registered hot-spot, and a button 1304 for use in deletion of the registered hot-spot. Further, there are provided an interface 1305 for use in selection of a chip for capturing an image of a selected hot-spot, an interface 1306 for use in displaying an image of the registered hot-spot, and information related thereto, and an interface 1307 for use in displaying a list of wafer coordinates of the hot-spot to be captured. Still further, the present interface is provided with a button 1309 for use in reading the list of the hot-spots registered before, a button 1310 for use in preservation of the list of the registered hot-spots, with names thereof attached thereto, and a button 1311 for use in cancellation of the hot-spot coordinate editing.

Figure 14:
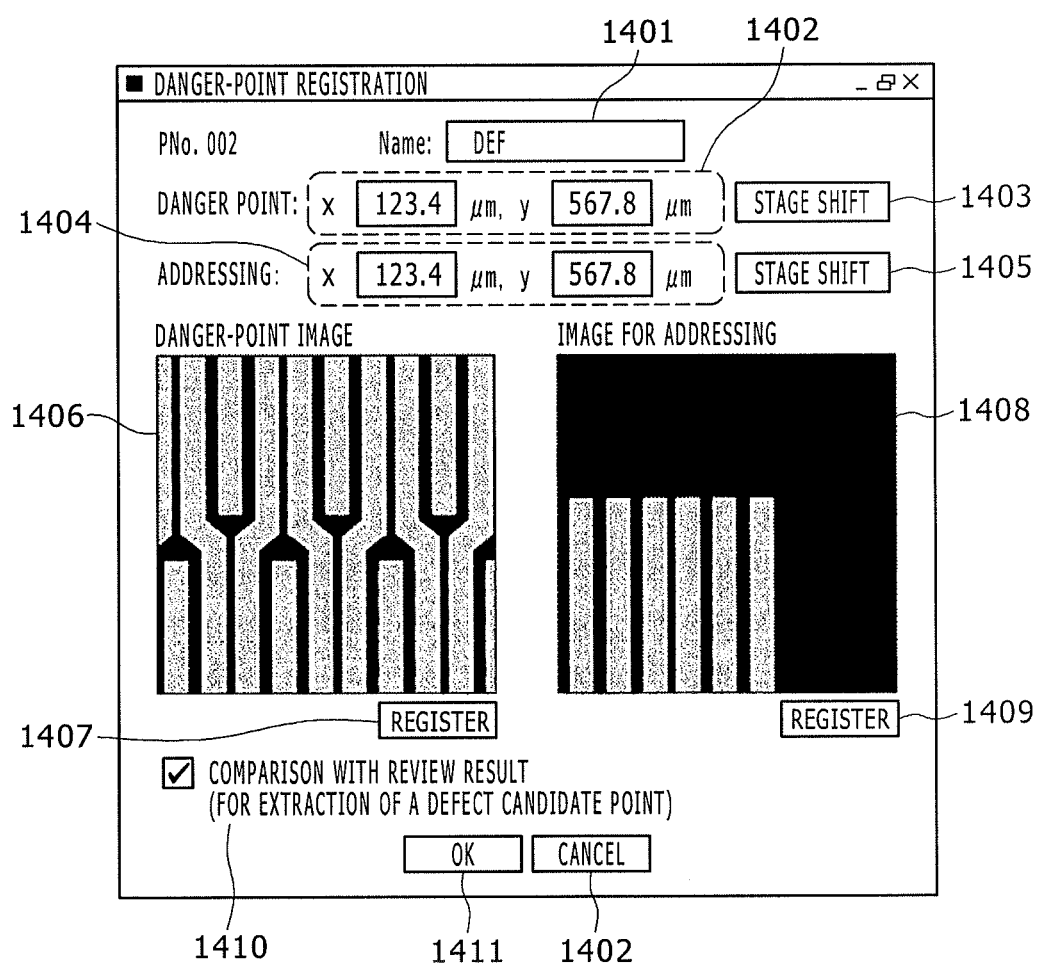
FIG. 14 is a view showing an example of an interface concerned with hot-spot registration.

FIG. 14 shows one example of an interface concerned with hot-spot registration. The present interface is called up by the "add" button 1302, or the "correct" button 1303, in the interface for the hot-spot coordinate editing. The present interface is provided with an interface 1401 for use in inputting an optional name in the hot-spot, an interface 1402 for use in inputting the coordinates of an hot-spot, a button 1403 for use in shifting the stage to inputted coordinates of the hot-spot, an interface 1404 for use in inputting of addressing coordinates, an interface 1405 for use in shifting the stage to addressing coordinates, an interface 1406 for use in displaying the image of an hot-spot, a button 1407 for use in registration of a hot-spot, an interface 1408 for use in displaying an addressing image, and a button 1409 for use in registration of the addressing image. Further, the present interface is provided with an interface for use in designating whether or not use is made for comparison with a defect review result in the step S1009. Furthermore, there are provided a button 1411 for use in completing a registration operation, and a button 1412 for use in interruption of the registration operation.

Figure 15:
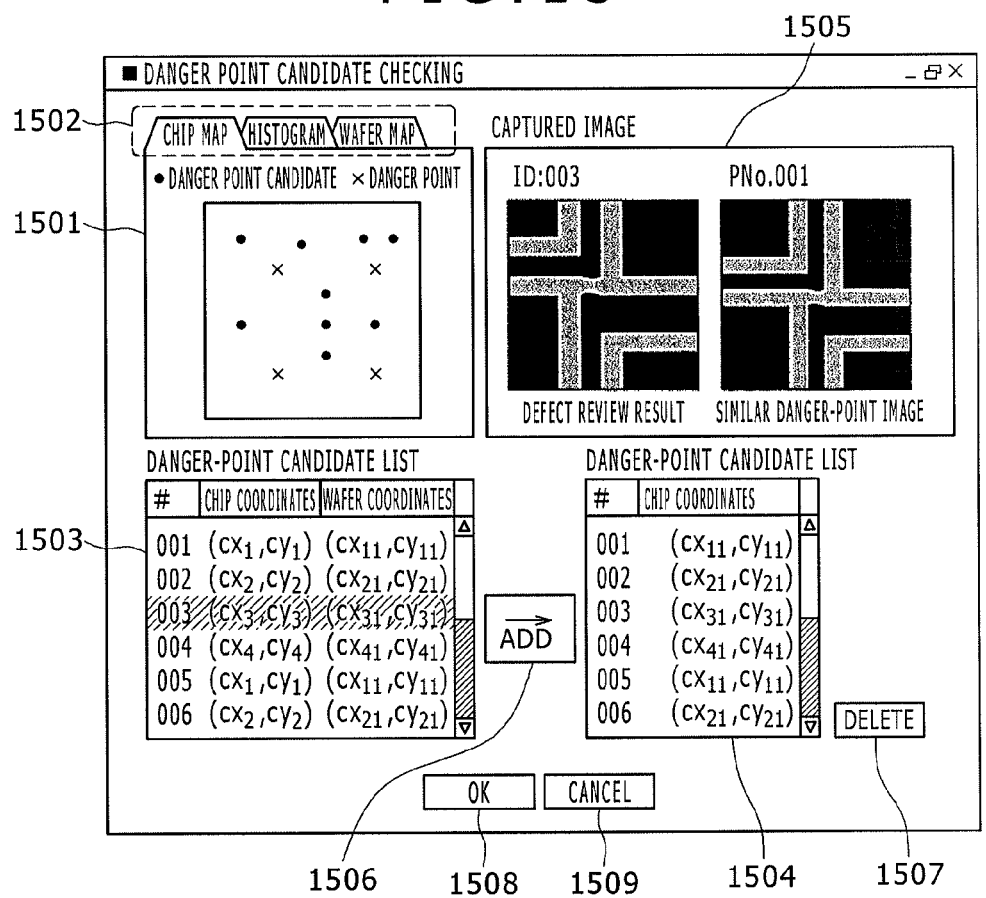
FIG. 15 is a view showing an example an interface for use in checking of hot-spot candidates.
Figure 16A:
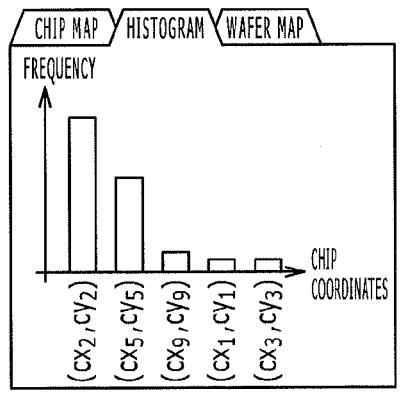
FIGS. 16A and 16B show an example of a method for mapping the hot-spot candidates.
Figure 16B:
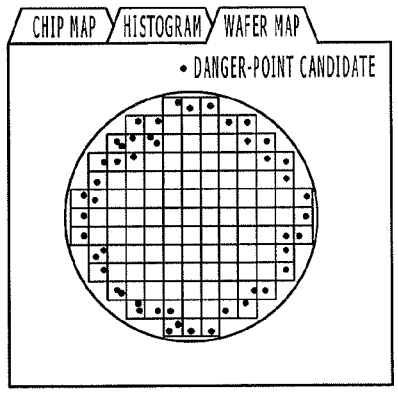

FIG. 15 shows an interface for use in checking of hot-spot candidates as extracted. The present interface is called up by the hot-spot candidate checking button 1211 of the interface concerned with setting of the recipe. The present interface is provided with an interface 1501 for use in mapping of the coordinates of a hot-spot candidate, and a hot-spot to be displayed, an interface 1502 for use in changeover of a mapping method, an interface 1503 for use in displaying a list of extracted hot-spot candidates, an interface 1504 for use in displaying a list of registered hot-spots, and an interface 1505 for use in displaying images concerning selected hot-spot candidates, and design information corresponding thereto. Further, there are provided a button 1506 for use in adding a selected hot-spot candidate as a hot-spot, a button 1507 for use in deletion of a registered hot-spot. Still further, there are provided a button 1508 for use in completing a checking operation, and a button 1509 for use in interrupting the operation. With the use of the present interface, a user can get hold of hot-spots within a chip. Further, as a method for displaying the hot-spot candidates by mapping, extraction frequency of hot-spots for every chip coordinate may be displayed in a graph as shown in FIG. 16A. By so doing, respective hot-spot candidates occurring to many chips can be grasped with ease. And the hot-spot candidates may be displayed in a wafer map (refer to FIG. 16B). As a result, it becomes possible to get hold of distribution of respective chips where a hot-spot candidate is extracted in a wafer plane, thereby enabling guidelines for deciding a chip as an inspection target to be obtained.

Figure 17A:
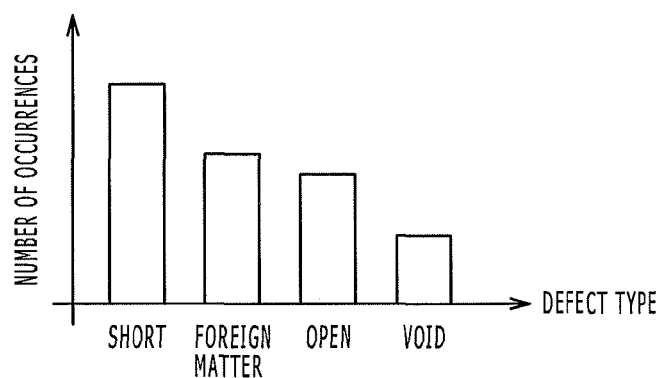
FIGS. 17A and 17B show an example of an output by summing up a result of the defect review, and a result of the hot-spot inspection.
Figure 17B:
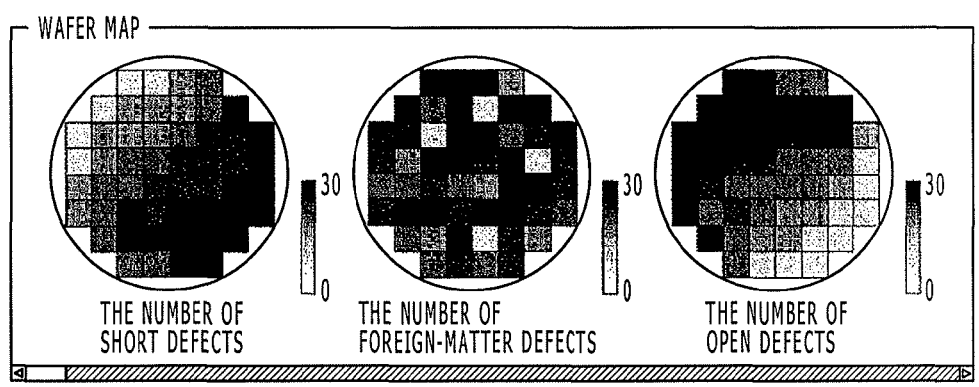

FIGS. 17A and 17B show an example of an output resulting from execution of the defect review, and the hot-spot inspection. It is possible to display occurrence frequency by the defect type (FIG. 17A), an occurrence tendency in a wafer plane by the defect type (FIG. 17B), and so forth.

As described in the foregoing, at the time of executing the defect review, and the hot-spot inspection, the hot-spot coordinates are merged with the detected defect coordinates after adding respective attributes thereto, and the captured-image sequence is set such that the shift distance of the stage can be rendered shorter, thereby executing image-capturing, while changing over the respective sequences according to the attributes added to the coordinates, respectively, whereupon sharing of the sequence of the wafer alignments, and the sequence of the focus map estimations is enabled, and stage-shift time can be reduced, so that the defect review, and the hot-spot inspection can be efficiently executed. Furthermore, an image high in coincidence with an image acquired by the hot-spot inspection is searched from the result of the defect review to extract a hot-spot candidate, thereby enabling a user to get hold of a location susceptible to occurrence of a systematic defect. Thus, the use of the present invention enables a user to more quickly get hold of the occurrence frequency by the defect type, and the occurrence tendency in the wafer plane with a higher accuracy, so that the user can quickly obtain guidelines for deciding process-improvement guidelines.

Second Embodiment

Figure 18:
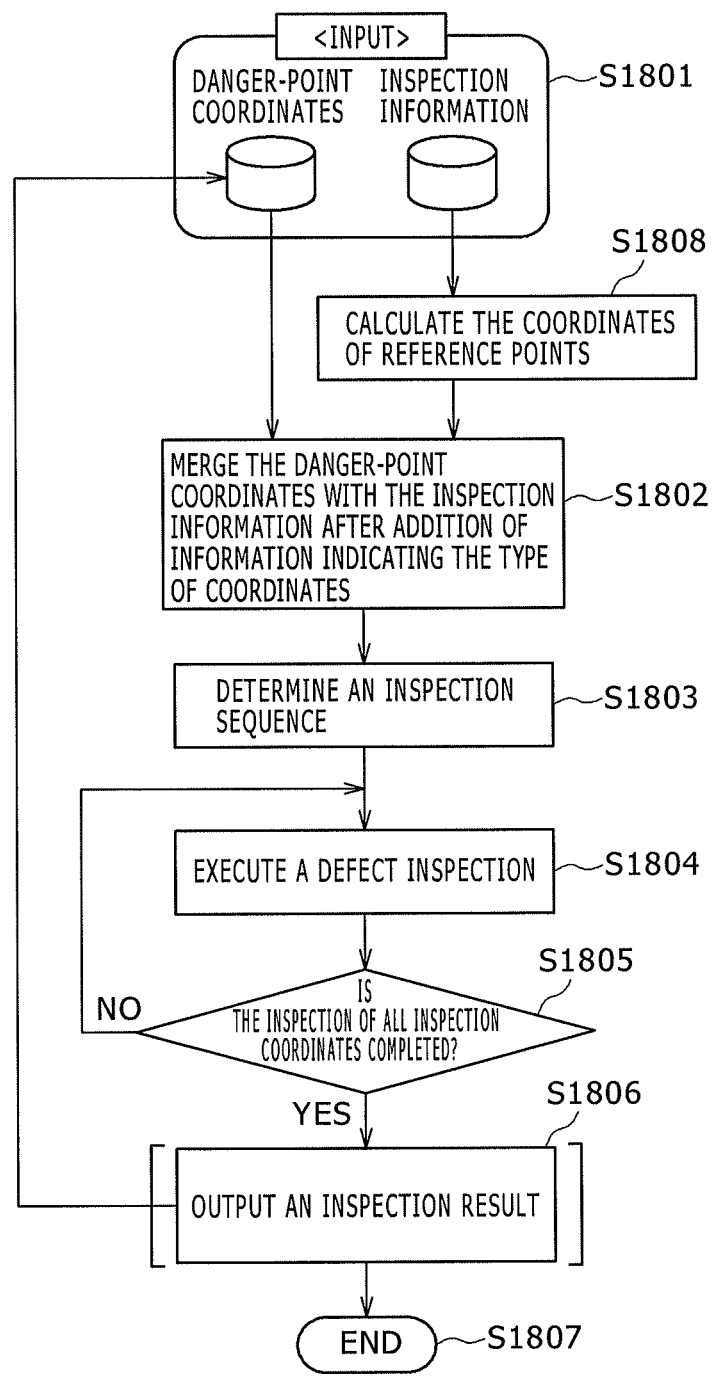
FIG. 18 is a flow chart of processing for a defect inspection.

FIG. 18 shows an inspection flow according to the invention. Hot-spot coordinates, and inspection information, that is, defect coordinates detected by the other inspection device, are inputted (step S1801). The inspection information may be inputted from a reader for reading information from an external storage unit such as a computer, a HDD (Hard Disk Drive), and so forth, a recording medium having portability, such as CD-ROM (Compact Disk Read Only Memory), and so forth, and communications equipment, and so forth. Next, the coordinates of reference points corresponding to respective defect-points included in the inspection information are worked out (step S1808). The hot-spot coordinates are merged with the inspection information after adding information indicating the type of coordinates to both thereof (step S1802). Subsequently, a captured-image sequence is rearranged (step S1803), and a defect inspection is executed according to a captured-image sequence (step S1804). Whether or not the inspection of all inspection coordinates is completed is checked (step S1805), and if so, an inspection result is outputted (step S1806), thereby completing the inspection (step S1807).

With a second embodiment of the invention, in particular, there is described hereinafter the information indicating the type of coordinates. In the step S1801, coordinates that are empirically judged, and decided by a user may be inputted as the hot-spot coordinates. The hot-spots may be worked out on the basis of an inspection result outputted from the other inspection device to be reflected on the inspection information. Or hot-spots as predicted on the basis of design data on a semiconductor wafer may be inputted.

In order to calculate the coordinates of the reference points in the step (S1808), it need only be sufficient to calculate coordinates designed such that a circuit pattern identical to that of the defect-point is formed. As the simplest method, it need only be sufficient to calculate coordinates corresponding to a defect-point in a die adjacent to a die where a defect-point is present. In other words, it need only be sufficient to increase, or decrease the coordinates of a defect-point, in magnitude, by the magnitude corresponding to one chip size. Further, an adjacent die is unnecessary, and reference point coordinates on a wafer may be worked such that a captured image thereof can be taken in the vicinity of the inputted hot-spot coordinates, or the inputted defect-point coordinates, or the reference point coordinates as already worked out. As described later on, an attribute of "reference" is added to the reference point coordinates worked out as above, in the step S1802, and linkage information on a corresponding defect-point is stored as incidental information.

Figures 19, 20:
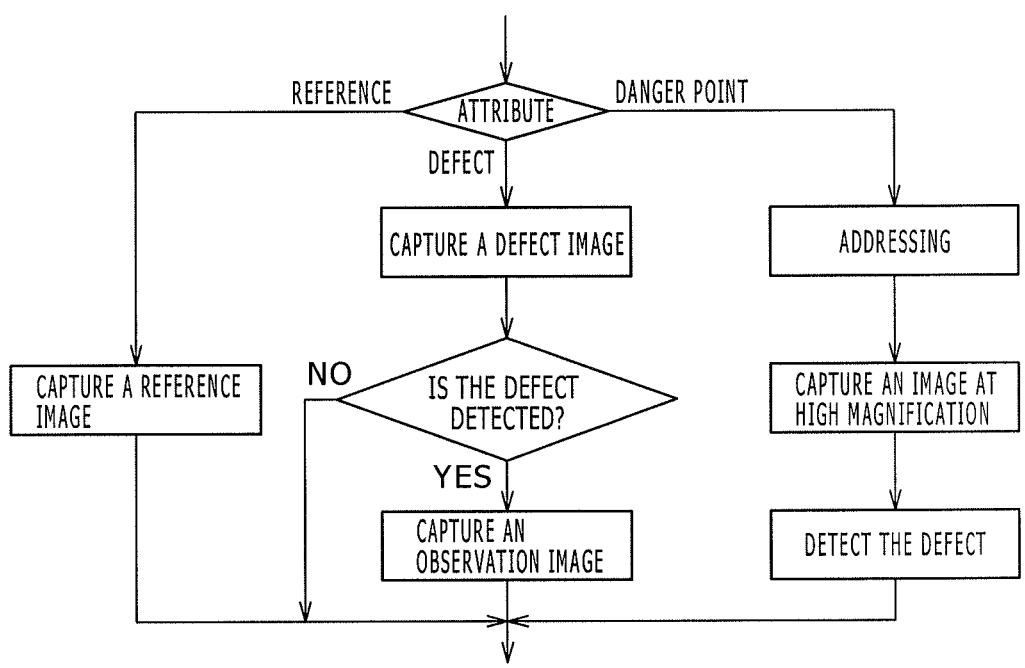
FIG. 19 is a view showing an example of information indicating the types of defects.
FIG. 20 is a flow chart of processing for the defect inspection (the defect review).

The merging between the hot-spot coordinates and the inspection information, in the step S1802, is described hereinafter with reference to FIG. 19. The information indicating the type of coordinates includes information such as information on the state or the type of a defect, information on inspection coordinates at the time of a defect inspection, information on an inspection method, and so forth. With the second embodiment, the information indicating the type of coordinates includes an attribute, a number as well as a name, indicating a defect, as necessary, with incidental information added thereto as shown in FIG. 19. The incidental information includes information for use in support of an inspection on a defect, linkage information on a defect-point corresponding to an inspection using a reference image, information indicating the state of a defect, information on defect occurrence probability, and so forth.

In the step S1803, a method for determining the captured-image sequence is the same as in the case of the first embodiment. Otherwise, captured-image sequence may be decided such that the inspection time can be shortened by taking not only the attribute of the inspection coordinates but also the shift-time of the stage up to the reference coordinates.

The defect inspection in the step S1804 is described with reference to FIG. 20. In the case of the attribute being a defect as shown in FIG. 19, a defect-image of inspection coordinates is captured, and a defect detection is executed on the basis of the captured-image of the inspection coordinates. In the defect detection, incidental information may be referred to, and a comparative inspection against a reference image as captured may be conducted to thereby find a defect, and in the case of, for example, a memory cell having repeat periodicity, a reference image may be synthesized from the defect image to thereby execute the comparative inspection.

The case of the attribute being "reference" is described hereinafter. The stage is shifted up to the reference image to thereby take a captured-image of the reference image.

The sequence in the case of the attribute being "reference" and "defect" is called an observation, and the sequence in the case of the attribute being "hot-spot" is called hot-spot inspection, or simply as an inspection.

In the case of the attribute being "hot-spot", the stage is shifted to the hot-spot coordinates referred to (addressing), and the inspection is conducted by taking a captured-image of the hot-spot coordinates.

In other words, after making a judgment on the information indicating the type of coordinates, the inspection or the observation is conducted, while changing over between the inspection sequences according to the type of the coordinates.

As described in the foregoing, at the time when the defect review, and the hot-spot inspection are executed, the hot-spot coordinates are merged with the inspection information after adding the information indicating the type of the coordinates thereto, the captured-image sequence is decided, and the inspection or the observation is carried out, while changing over between the sequences according to attributes, in particular, included in the information indicating the type of coordinates, whereupon the sharing of the sequence of the wafer alignments, and the sequence of the focus map estimations is enabled, and the stage-shift time can be reduced, so that the defect review (the observation), and the hot-spot inspection can be efficiently executed. Further, the image high in coincidence with the image acquired by the hot-spot inspection is searched on the basis of the result of the defect review to extract the hot-spot candidate, thereby enabling a user to get hold of the location susceptible to occurrence of the systematic defect. Therefore, the use of the present invention enables a user to more quickly get hold of the occurrence frequency by the defect type, and the occurrence tendency in the wafer plane with a higher accuracy, so that the user can quickly obtain the guidelines for deciding the process-improvement guidelines.

What is claimed is:

1. A method for inspecting a semiconductor, comprising:
   merging first coordinates and second coordinates of locations on the semiconductor, wherein the first coordinates and the second coordinates have respective coordinate type information, the first coordinates are hot-spot coordinates where a systematic defect can occur, and the second coordinates are defect coordinates of the semiconductor;
   deciding an inspection sequence of the merged coordinates; and
   inspecting the merged coordinates using a selected inspection method that is selected from a plurality of different inspection methods based on the respective coordinate type information.

2. The method according to claim 1,
   wherein the inspection sequence is decided based on moving time of a stage located under the semiconductor.

3. The method according to claim 1,
   wherein the different inspection methods are a first inspection method to inspect the first coordinates and a second inspection method to inspect the second coordinates.

4. The method according to claim 1, further comprising obtaining a coincidence value of a first image of the first coordinates and a second image of the second coordinates.

5. The method according to claim 4 further comprising comparing the coincidence value and a predetermined value.

6. The method according to claim 5, further comprising changing type information of the second coordinates to type information of the first coordinates based on a result of the comparing the coincidence value and the predetermined value.

7. The method according to claim 4,
   wherein type information of the first coordinates is systematic defect, and
   wherein the second coordinates are obtained in advance by another inspection system.

8. The method according to claim 4, wherein the second coordinates are picked up as candidates of the hot-spot coordinates in case the coincidence value is high.

9. The method according to claim 1, further comprising steps of capturing a reference image, capturing a defect image of the second coordinates, detecting a defect site by comparing the reference image and the defect image, and capturing an observation image.

10. The method according to claim 1, further comprising steps of capturing an image of a hot-spot in the semiconductor, detecting a defect, and classifying the defect.

11. A device for inspecting a semiconductor, comprising:
    an operation unit that merges first coordinates and second coordinates of locations on the semiconductor, wherein the first coordinates and the second coordinates have respective coordinate type information, the first coordinates are hot-spot coordinates where a systematic defect can occur, and the second coordinates are defect coordinates of the semiconductor, and decides an inspection sequence of the merged coordinates; and
    a control unit that inspects the merged coordinates using a selected inspection method that is selected from a plurality of different inspection methods based on the respective coordinate type information.

12. The device according to claim 11,
    wherein the inspection sequence is decided based on moving time of a stage located under the semiconductor.

13. The device according to claim 11,
    wherein the different inspection methods are a first inspection method to inspect the first coordinates and a second inspection method to inspect the second coordinates.

14. The device according to claim 11, wherein the operation unit obtains a coincidence value of a first image of the first coordinates and a second image of the second coordinates.

15. The device according to claim 14, wherein the operation unit compares the coincidence value and a predetermined value.

16. The device according to claim 15, wherein the operation unit changes type information of the second coordinates to type information of the first coordinates based on a result of the comparing the coincidence value and the predetermined value.

17. The device according to claim 14,
    wherein type information of the first coordinates is a systematic defect, and
    wherein the second coordinates are obtained in advance by another inspection system.

18. The device according to claim 14, wherein the second coordinates are picked up as candidates of the hot-spot coordinates in case the coincidence value is high.

19. The device according to claim 11, wherein the operation unit captures a reference image, captures a defect image of the second coordinates, detects a defect site by comparing the reference image and the defect image, and captures an observation image.

20. The device according to claim 11, wherein the operation unit captures an image of a hot-spot in the semiconductor, detects a defect, and classifies the defect.

* * * * *